United States Patent [19]
Nabai et al.

[11] Patent Number: 5,394,886
[45] Date of Patent: Mar. 7, 1995

[54] SKIN BIOPSY PLUG AND METHOD

[76] Inventors: Hossein Nabai, 14555 Levan Rd., Suite 410, Livonia, Mich. 48154; Homayoon Rahbari, 1314 N. Macomb St., P.O. Box 360, Monroe, Mich. 48161

[21] Appl. No.: 123,679

[22] Filed: Sep. 20, 1993

[51] Int. Cl.$^6$ .............................. A61B 10/00
[52] U.S. Cl. ...................... 128/754; 604/265
[58] Field of Search .............. 128/749, 753, 754; 604/15, 265; 606/108, 167, 170

[56] References Cited

U.S. PATENT DOCUMENTS

| | | |
|---|---|---|
| 363,538 | 5/1887 | Penny . |
| 3,566,871 | 3/1971 | Richter et al. . |
| 4,409,206 | 10/1983 | Stricker . |
| 4,605,005 | 8/1986 | Sheehan . |
| 5,080,655 | 1/1992 | Haaga ........................ 604/265 |
| 5,275,616 | 1/1994 | Fowler ........................ 606/213 |

*Primary Examiner*—Max Hindenburg
*Attorney, Agent, or Firm*—Alex Rhodes

[57] ABSTRACT

A plug and method for controlling bleeding and repairing a circular wound caused by the excising of a specimen of skin from a patient with a biopsy punch. The plug is a cylindrical porous sponge made from a gelatin material which, when implanted into a wound, swells, absorbs blood and is completely absorbed by the patient with little tissue reaction. By completely filling the bleeding site, the plug promotes healing without the necessity of suturing. In the first aspect of the invention, a sterile cylindrical plug is provided having about the same diameter as the biopsy punch used for excising the specimen. In a second aspect of the invention, after a specimen has been excised with a biopsy punch, the cylindrical plug is cut from a pad of the gelatin material with the same punch and implanted into the wound.

9 Claims, 1 Drawing Sheet

SKIN BIOPSY PLUG AND METHOD

FIELD OF THE INVENTION

This invention relates to surgical implants and more particularly to a plug and method for controlling bleeding and repairing a wound caused by the excising of a specimen of skin with a circular biopsy punch.

BACKGROUND OF THE INVENTION

A skin biopsy is a well known medical procedure for diagnosing skin disorders. A small cylindrical specimen of skin is excised with a cylindrical knife, commonly referred to as a biopsy punch for analysis in a pathology laboratory. After the specimen has been excised, the wound is repaired with sutures or butterfly bandages.

The difficulties with repairing a wound with sutures or butterfly bandages is that there is a likelihood of inducing excessive scar tissue and that some patients suffer anxiety during suturing of wounds.

In our co-pending applications Ser. Nos. 08/056,399 and 08/088,678, novel devices and methods, employing cylindrical gelatin sponges for repairing biopsy sites after the excising of skin biopsy specimens.

SUMMARY OF THE INVENTION

The present invention is directed to a small cylindrical plug for repairing a biopsy which itself is believed to be novel and a method based on the cylindrical plug.

In the first aspect of the invention a cylindrical plug is provided having the same diameter as the usual cylindrical punch used by a physician for excising a biopsy specimen. The plug is preferably made from an open cell gelatin sponge which is completely absorbed by a patient with little tissue reaction. When the plug is implanted into the cylindrical bleeding site, the plug completely fills the wound, absorbs blood, swells and terminates the flow of blood in the bleeding site.

By completely filling the bleeding site, the plug controls bleeding and promotes healing without the necessity of suturing. In a second aspect of the invention the cylindrical plug is cut from a pad of the gelatin sponge after the specimen has been excised with a punch and implanted into the wound.

In each aspect, after the plug is implanted into a wound, pressure is applied to the plug for about thirty to sixty seconds until bleeding stops.

Further features and benefits of our invention, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

DETAILED DESCRIPTION OF THE PREFERRED EMBODIMENT

Figure 1:
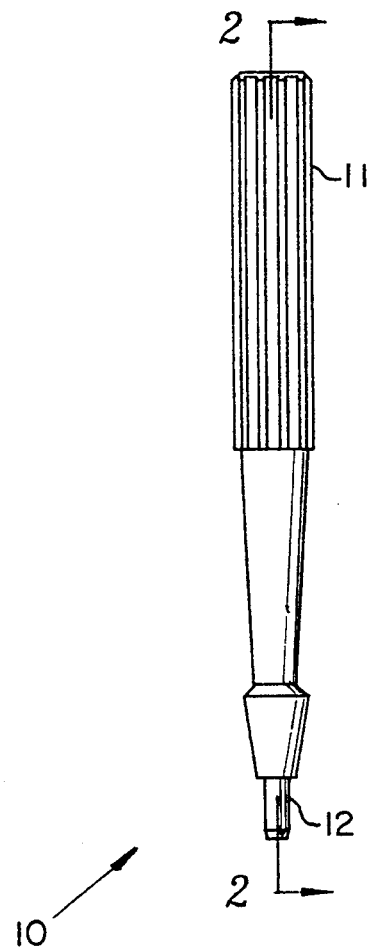
FIG. 1 is a front view of a usual skin biopsy punch of the prior art.
Figure 2:
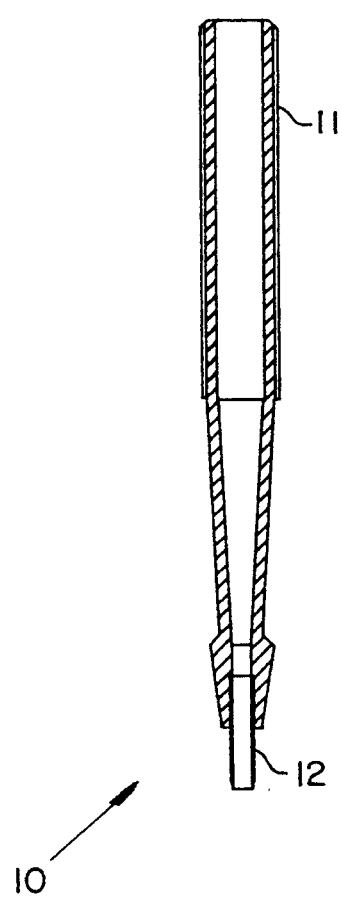
FIG. 2 is a cross-sectional view taken on the line 2—2 in FIG. 1.

Referring now to the drawings wherein like numerals designate like and corresponding parts throughout the several views, in FIGS. 1 and 2, a prior art punch 10 is shown for excising a small diameter specimen of skin. The punch consists of a tubular plastic handle 11 and a thin sharp cylindrical blade 12 attached to one end of the handle 11. Punches, ranging in diameter from two to six millimeters, are commonly used to excise small samples of skin for medical biopsies.

The thin sharp blade 12 is pressed against the skin and rotated to excise a cylinder shaped sample for a biopsy. After the specimen has been excised, bleeding must be controlled and the circular wound caused by removal of the specimen must be repaired.

Figure 3:
FIG. 3 is a plan view drawn to an enlarged scale of a pre-cut cylindrical implant having the same diameter as a skin specimen taken with the punch shown in FIG. 1.
Figure 4:
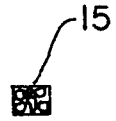
FIG. 4 is a front view of the implant.

With reference to FIGS. 3 and 4, a small cylindrical plug 13 for controlling bleeding and repairing the wound is shown, according to the invention. The plug 13 is a cylindrical open cell sponge about three millimeters thick having the same diameter as the cylindrical blade 12 of the biopsy punch 10 which was used by a physician for excising the specimen. The plug is preferably cut or molded from a water-insoluble, porous gelatin material which is absorbed completely by a patient with little tissue reaction.

When the sponge is implanted into the bleeding site, the plug absorbs blood, swells and terminates the flow of blood. By sizing the plug such that it completely fills the biopsy site, the plug controls bleeding and promotes healing without the necessity of suturing.

One material which was evaluated and found to be acceptable is an absorbable gelatin sponge marketed by the Upjohn Company under the trademark "GEL-FOAM". It is a water-insoluble, off-white, non-elastic, porous, pliable material made from purified pork skin gelatin USP granules and is available in the form of pads.

The manner of using our invention is as follows. After a biopsy specimen has been excised, the cylindrical plug 13 is positioned over the wound at the biopsy site and implanted into the wound with a device such as the usual pair of forceps. Thereafter pressure is applied to the sponge with a fiber cotton wad for approximately thirty to sixty seconds to seal the wound and stop bleeding.

After the bleeding has stopped, a topical antibiotic ointment such as Bacitracin or Bactoroban is applied to the biopsy site and a conventional sterile dressing (not shown) is applied over the ointment. The dressing is removed after approximately twenty-four hours. The wound site may need to be cleaned twice a day with rubbing alcohol or a hydrogen peroxide solution until healing has been completed.

Figure 5:
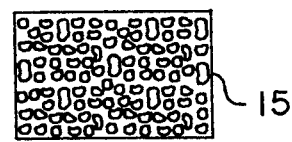
FIG. 5 is a plan view of a thin pad of the same material as the implant shown in FIG. 3.
Figure 6:
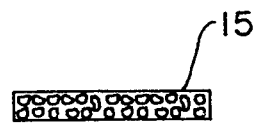
FIG. 6 is a front view of the pad.

Referring now to FIGS. 5 and 6, in the second aspect 14 of the invention, after the specimen has been excised, the small cylindrical plug 13 is cut with the punch 10 which was used for excising the biopsy specimen from a rectangular pad 15 about three millimeters thick made from the same material as the previously described embodiment.

From the foregoing it will be understood that our invention provides an effective, easy to use plug and method for controlling bleeding and repairing a wound caused by the excising of a specimen of skin with a biopsy punch.

Although only several embodiments have been disclosed, it is not our intention to limit our invention to these embodiments since other embodiments can be developed by persons skilled in the art without departing from the spirit thereof.

We claim:

1. The combination of a circular biopsy punch having a thin sharp cylindrical blade ranging in diameter from about two to six millimeters for excising a skin specimen from a patient and a thin cylindrical plug having about the same diameter as said punch for controlling bleeding and repairing a wound caused by the excising of said specimen, said plug being implanted into said wound after said excising of said specimen.

2. The combination as recited in claim 1 wherein said plug is made from a material which, when implanted into said wound, swells, absorbs blood and is absorbed completely by said patient.

3. The plug as recited in claim 1 wherein said sponge is a porous and pliable product made from purified pork skin.

4. A method for controlling bleeding and repairing a circular wound caused by the excising of a specimen of skin from a patient with a circular biopsy punch of about two to six millimeters in diameter comprising the step of implanting into said wound a thin cylindrical plug made from porous sponge of a gelatin material of about two to six millimeters in diameter which, when implanted into said wound, swells, absorbs blood and is completely absorbed by said patient.

5. A method for controlling bleeding and repairing a wound caused by the excising of a specimen of skin of about two to six millimeters in diameter from a patient with a circular biopsy punch comprising the step of cutting with a biopsy punch of about two to six millimeters in diameter a cylindrical plug from a porous sponge pad of a gelatin material which, when implanted into said wound, swells, absorbs and is completely absorbed by said patient; and implanting said cylindrical plug into said wound caused by said excising of said specimen.

6. The method recited in claim 5 further comprising the step of applying pressure to said sponge for thirty to sixty seconds after said sponge has been implanted into said wound.

7. The method recited in claim 5 further comprising the step of applying a topical antibiotic ointment to said sponge and the area surrounding said sponge after bleeding has been controlled.

8. The method recited in claim 7 further comprising the step of applying a dressing over said excised area after said topical ointment has been applied.

9. The method recited in claim 8 further comprising the steps of removing said dressing and cleaning said excised area twice a day with rubbing alcohol or a hydrogen peroxide solution until healing has been completed.

* * * * *